(12) United States Patent
Chor

(10) Patent No.: US 7,511,283 B2
(45) Date of Patent: Mar. 31, 2009

(54) ULTRAVIOLET DISINFECTION DEVICE

(76) Inventor: Yue Lai Chor, Unit 908, Shui Hing Centre, 13 Sheung Yuet Road, Kowloon Bay, Kowloon (HK)

(*) Notice: Subject to any disclaimer, the term of this patent is extended or adjusted under 35 U.S.C. 154(b) by 109 days.

(21) Appl. No.: 11/518,293

(22) Filed: Sep. 8, 2006

(65) Prior Publication Data

US 2007/0057197 A1    Mar. 15, 2007

(30) Foreign Application Priority Data

Sep. 9, 2005    (HK) .................................. 1075576

(51) Int. Cl.
    *H01J 37/20*    (2006.01)
(52) U.S. Cl. .................... 250/455.11; 250/454.11; 250/453.11; 250/504 R; 250/504 H
(58) Field of Classification Search ............ 250/453.11, 250/454.11, 455.11, 504 R, 504 H
    See application file for complete search history.

(56) References Cited

U.S. PATENT DOCUMENTS 4,045,680 A * 8/1977 Loher ..................... 250/504 R
6,132,784 A  10/2000 Brandt et al.
2004/0025899 A1* 2/2004 Pinsky ........................ 132/310

FOREIGN PATENT DOCUMENTS

CN      2253983 Y    5/1997
CN       328474 A   12/2001

OTHER PUBLICATIONS

English-language translation of the first page Search Report by SIPO with an English-language translation.

* cited by examiner

*Primary Examiner*—Jack I Berman
*Assistant Examiner*—Michael Maskell
(74) *Attorney, Agent, or Firm*—Law Office of Sergei Orel, LLC

(57) ABSTRACT

The invention relates to a UV-lamp sterilizing appliance that is used to destroy bacteria. The appliance presents a simple design which can facilitate the sterilization of any elongate personal article such as toothbrush, chopsticks and the like for sanitation by simply putting them into the appliance. The appliance also includes a protective shield surrounding the UV-lamp. The shield is designed to prevent any damage to the user's sight from the leakage of the UV-lamp radiation and also to retain the capacity to destroy bacteria sufficiently. The shield also protects the lamp from damage. Thereby the appliance according to the invention can be used easily and safeguards the user's health.

5 Claims, 8 Drawing Sheets

ULTRAVIOLET DISINFECTION DEVICE

TECHNICAL FIELD OF THE INVENTION

This invention is a disinfection device, to be specific, an Ultraviolet Disinfection Device that uses ultraviolet light to kill germs and includes a protective shield.

BACKGROUND OF THE INVENTION

It is well known that ultraviolet (a.k.a. UV) light of a particular range of wavelength, called germicidal UV light, can destroy germs. The Ultraviolet Disinfection Device of the present invention is a device that kills germs by means of the germicidal UV light that is generated by the ultraviolet lamp. Elongated personal articles, such as toothbrush and chopsticks, can be disinfected by inserting them into the device.

Currently, there are two types of ultraviolet disinfection devices for disinfecting long objects such as toothbrushes and chopsticks. One type uses an enclosed case, with several hooks or other fixtures inside for hanging or holding the objects to be disinfected. The user only need to place the objects properly, close the cover, and turn on the ultraviolet lamp. Disinfection is achieved by illuminating the objects to be disinfected for a certain period of time with the ultraviolet light that is generated by the ultraviolet lamp inside the device. Although this type of device can disinfect effectively, it is not convenient. The user has to spend time opening and closing the cover, as well as hanging or placing the objects properly. The other type of device, which is more popular, uses a simpler design. By inserting the objects to be disinfected into the disinfecting cells of the device through the openings on the top cover of the device, the portions of these objects that are exposed to the ultraviolet light can be disinfected. But that introduces another more serious issue that concerns safety. Since ultraviolet light can leak from the holes through which the objects are inserted for disinfection, it can hurt the eyes of the user if the user looks into the ultraviolet lamp of the device through those holes.

In view of the above, it is apparent that there exists a need for an ultraviolet disinfection device that provides effective disinfection and is both convenient and safe to use. This invention addresses this need.

OBJECTIVES AND SUMMARY OF THE INVENTION

The primary objective of the present invention is to provide an ultraviolet disinfection device for effective disinfection of objects such as toothbrushes and chopsticks. Another objective is to provide an ultraviolet disinfection device that is both convenient and safe to use. It can both tremendously reduce leakage of the ultraviolet light, thus protecting the user's eyes, and yet maintains good disinfection capability.

The above objectives can be accomplished in the ultraviolet disinfection device of this invention. The most salient feature of this ultraviolet disinfection device is the protective shield which surrounds the ultraviolet lamp that generates the germicidal UV light. The said protective shield provides two protective functions. Firstly, it protects the user's eyes by preventing the ultraviolet light generated by the ultraviolet lamp from leaking directly through the openings of the top cover of the ultraviolet disinfection device. Secondly, it protects the ultraviolet lamp, which it surrounds, from being damaged by mechanical forces exerted by any object that is inserted in any of the disinfection cells of the ultraviolet disinfection device.

A preferred embodiment of the ultraviolet disinfection device of the present invention can be illustrated as comprising the following major components:

A base that is at the bottom of the ultraviolet disinfection device. At the bottom of this base is a base bottom cover. Above this base bottom cover is a circuit board. Above this circuit board is a base body. The top surface of the base body is a platform from where supporting poles protrude upwards. There is a pushbutton switch on the base body and is connected to the circuit board that is inside the base.

A device body that is placed on top of the base body. This device body includes a base ring that is at the bottom of the device body, and a center shell that is on top of the base ring. The base ring is preferably translucent to visible light but opaque to UV light.

A reflection cup that is placed inside the device body. This reflection cup includes two connected portions: a reflection cup ring and a reflection cup body.

A top cover, which can be removable, that is above the reflection cup and on top of the center shell. This top cover contains disinfection cell holes, which are on top of the disinfection cells. Near the bottom rim of the top cover, there are locking hooks. From the bottom of the top cover near the disinfection cell holes, there are two triggering hooks protruding downwards.

A protective shield that is mounted on top of the supporting poles. It features (1) a shield body, preferably cylindrical, with a number of fixing arms protruding horizontally outwards from the top region of the outer surface of the cylindrical body, (2) a stack of horizontal slats, ring shaped if the shield is cylindrical, strategically deployed at non-uniform vertical spacing below the lower rim of the said cylindrical shield body and (3) a number of thin vertical links protruding downwards from the bottom circular rim of the said cylindrical shield body. The said horizontal, thin, ring-shaped circular slats are linked together and kept at strategic vertical spacing by the said thin vertical links.

A germicidal ultraviolet lamp that is fitted inside the shield body by means of a lamp holder.

A protective shield cover is on top of the shield body. It has the same shape as the top portion of the shield body including its fixing arms.

A mechanical triggering device that is placed inside one of the supporting poles. This triggering device includes a pivot supporting frame and a pivoted trigger plank.

By this simple design, this invention can conveniently disinfect personal belongings and promote personal hygiene by simply inserting any long objects such as toothbrushes and chopsticks into a disinfection cell of this device. Meanwhile, the protective shield that surrounds the ultraviolet lamp greatly reduces the leakage of ultraviolet light, thus preventing damage to the user's eyes. Yet it still provides enough disinfection power. Thus, in addition to the convenience of usage, this ultraviolet disinfection device also protects the user's health.

A preferred embodiment of the present invention is illustrated in the accompanying drawings and is now described in detail.

DETAILED DESCRIPTION OF THE INVENTION

The invention is illustrated through a description of a preferred embodiment in which the device is designed around a cylindrical protective shield. Please refer to FIG. 1 first. This figure shows the top view of this ultraviolet disinfection device 100. In this embodiment of the invention, there are four disinfection cells 35 and therefore four openings on the top cover of the device.

Figure 1:
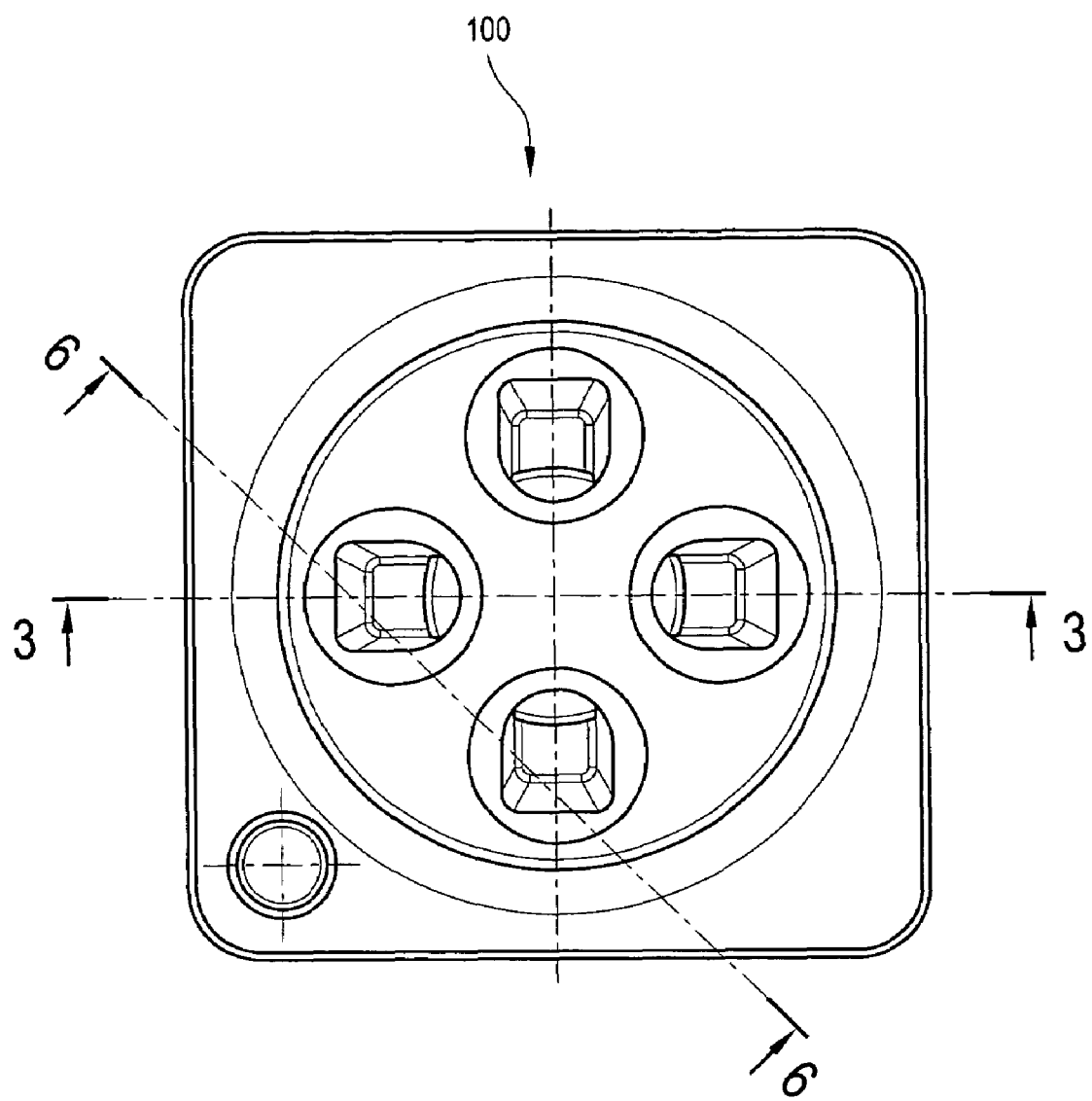
FIG. 1 is a top view of a preferred embodiment of this ultraviolet disinfection device.
Figure 2:
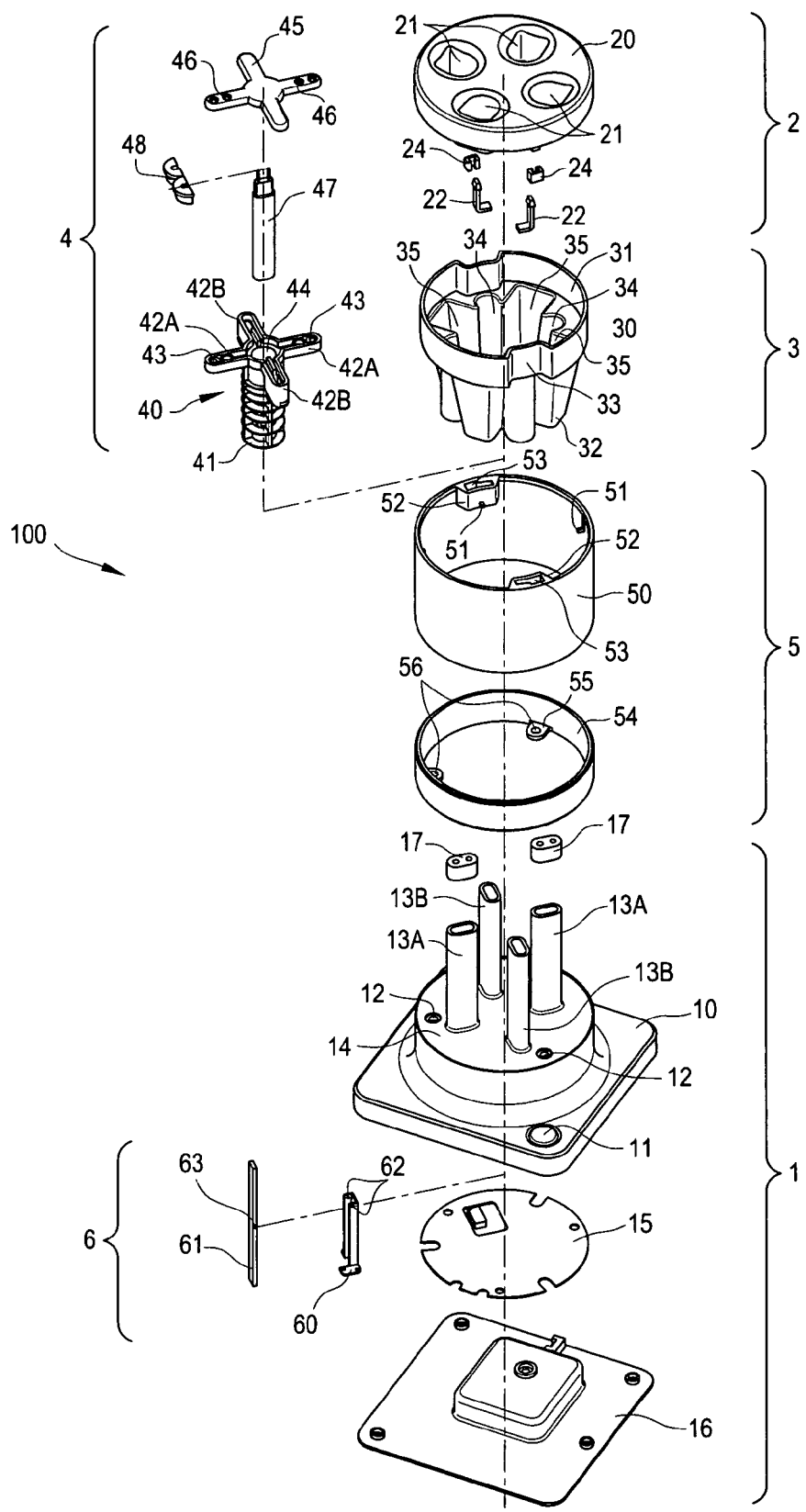
FIG. 2 is an exploded view of the ultraviolet disinfection device that is shown in FIG. 1.
Figure 3:
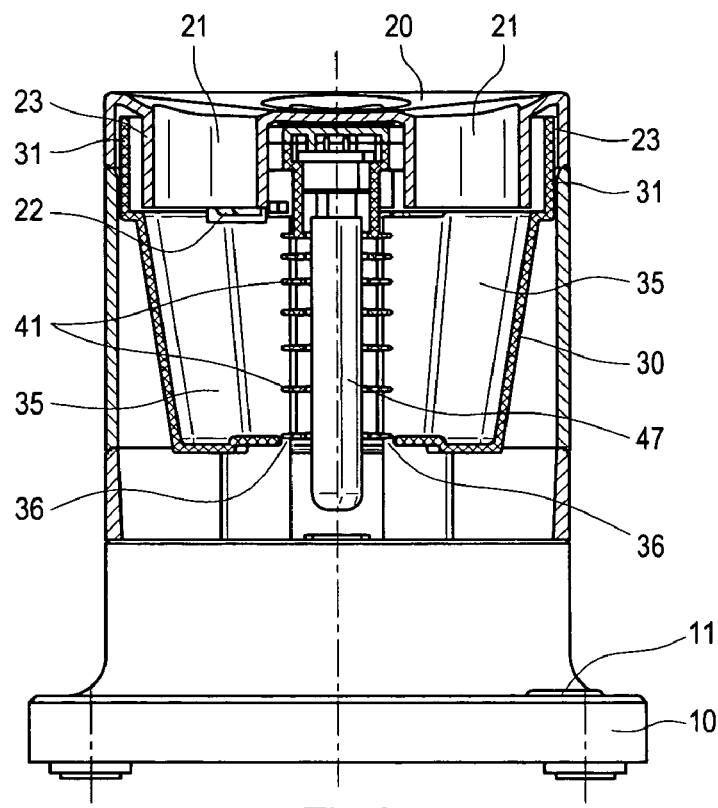
FIG. 3 is a sectional view along the axis 3-3 of FIG. 1.
Figure 6:
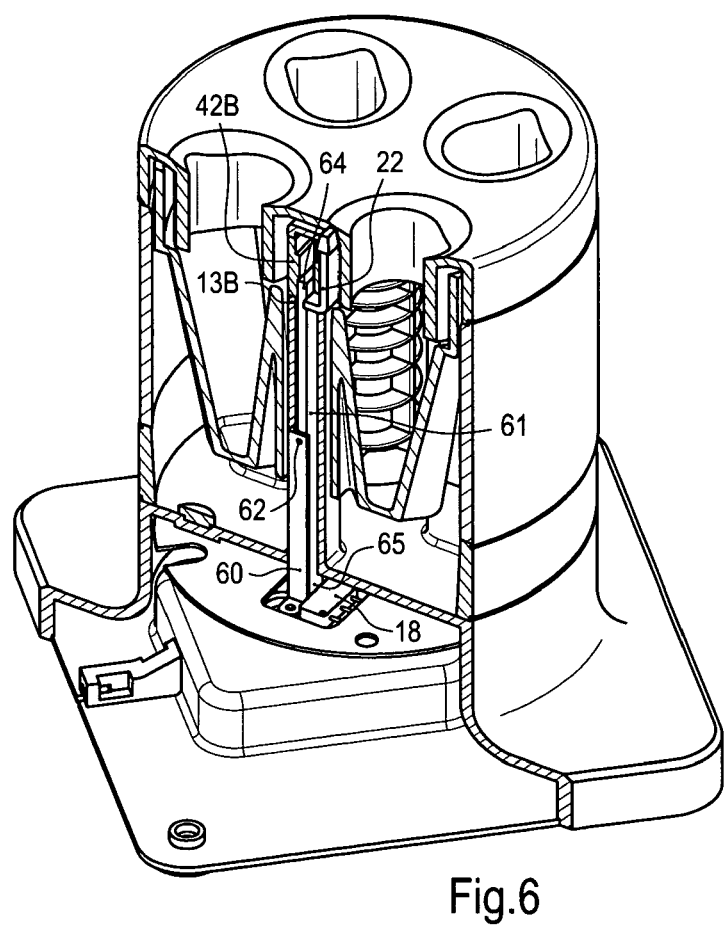
FIG. 6 is a perspective sectional view along the axis 6-6 of FIG. 1.

Please then refer to FIG. 2 and FIG. 3. FIG. 2 is an exploded view of the preferred embodiment of the ultraviolet disinfection device that is shown in FIG. 1. FIG. 3 is a sectional view along the axis 3-3 of FIG. 1. The device has a base 1 at the bottom of the ultraviolet disinfection device 100. At the bottom of base 1 is a base bottom cover 16. Above the base bottom cover 16 is a circuit board 15. There is a micro-switch 18 inside the base 1 (as shown in FIG. 6). The micro-switch 18 is connected to the circuit board 15. Above the circuit board 15 is a base body 10.

The top surface of the base body 10 is raised to form a platform 14. On the platform 14 there are two sets of supporting poles 13A and 13B. On top of each supporting pole 13A there is a supporting pole extension 17. Each supporting pole 13B has a triggering hook holding slot on the outer side of the top of supporting pole 13B. On the rim of the platform 14 there are several base connection holes 12 to connect to the base ring 54 that is placed inside of platform 14. In one corner of base body 10 there is a pushbutton switch 1I1 that is connected to the circuit board 15 that is placed inside base 1. A mechanical triggering device 6 is placed inside one of the supporting poles 13B. This mechanical triggering device 6 consists of a pivot supporting frame 60 and a trigger plank 61. The pivot supporting frame 60 is placed inside one of the supporting poles 13B. At the central part near the top edge of each of the two sides of the top portion of the pivot supporting frame 60 that are facing each other, there is a pivot hole 62. The two pivot holes 62 respectively on the said two opposite sides are in line. The two trigger plank pivot shafts 63 that protrude from the central part of the two narrower sides of the trigger plank 61 is respectively engaged into the two pivot holes 62. Thus, the trigger plank 61 can turn about the axis of the pivot.

A device body 5 is installed on top of base body 10. This device body 5 includes a base ring 54 that is at the bottom of device body 5 and a center shell 50 that is on top of base ring 54. Base ring 54 is made of a material that is preferably translucent to visible light but opaque to UV light. The footprint of center shell 50 and base ring 54 matches the shape of the round platform 14 that is on top of base body 10. Thus after they are attached together and aligned, base 1 and device body 5 can be connected together by inserting screw bolts through the base ring connection hole 56 inside the base ring fixing block 55 on the rim of the base ring 54, and through the base connection hole 12 on the platform 14.

Furthermore, the preferred embodiment includes several cover lockers 52 intruding inside, as well as several slightly bulging reflection cup supporters 51 on the inner surface of the centre body 50 near the top. In the middle of each cover locker 52 there is a cover locking slot 53. Reflection cup supporter 51 is used to hold reflection cup 3 to mount it inside device body 5. Cover locking slot 53 is an irregular slot. One end of the slot is wider than the other. Thus the locking hook 24 beneath the top cover 2 can be placed inside it to lock the top cover 2 on top of the device body 5. The reflection cup 3 is installed inside device body 5. The reflection cup unit 30 has two connected portions: reflection cup ring 31 and reflection cup body 32. Reflection cup ring 31 is a cylinder with two indentations on its surface at the opposite ends of a diameter of the reflection cup 31. The two indentations form two reflection cup notches 33, which engage with the two intruding cover lockers 52 on the top portion of the center body 50. On the bottom of the reflection cup body 32 there is a cross-shaped, in this embodiment, hole which is the supporting pole passage hole 36 (as shown in FIG. 3).

When the reflection cup 3 is installed into the device body 5, the supporting poles 13A and 13B pass through the supporting pole passage hole 36 to fit into the supporting pole holding cavities 34 inside the reflection cup body 32. The space between these supporting pole holding cavities 34 are disinfection cells 35. The objects to be disinfected will be placed here for disinfection.

In a preferred embodiment, an ultraviolet protective shield 4 comprises (a) a shield body 40, in this embodiment it is cylindrical, with four fixing arms 42A and 42B protruding horizontally from the top region of the outer surface of the cylindrical body to form a cross shape as view from above, (b) a stack of horizontal, ring-shaped, preferably thin, circular slats 41 strategically deployed at non-uniform vertical spacing below the lower circular rim of the shield body 40 and (c) a number of vertical links, preferably thin, protruding downwards from the bottom circular rim of the shield body 40. The various levels of horizontal circular slats 41 are linked together and kept at strategic vertical spacing by the said vertical links. The four fixing arms 42A and 42B of the protective shield 4 are mounted on top of the four supporting poles 13A and 13B, respectively, with the supporting pole extensions 17 priorly glued on top of the supporting poles 13A, as extended parts of supporting poles 13A.

The ultraviolet lamp 47 has its two adjacent electrodes located at one end. Each electrode has a connecting wire. Lamp holder 48 embraces the top part of the ultraviolet lamp and its two electrodes. The lamp holder 48, together with the ultraviolet lamp 47, is inserted and fitted into the hollow center of the shield body 40 of the ultraviolet protective shield 4, with the whole length of the ultraviolet lamp 47 being surrounded by the stack of slats 41 of the ultraviolet protective shield 4. The two connecting wires of the ultraviolet lamp 47 are threaded through the central cavity of one of the supporting pole 13B to reach the circuit board 15 from where suitably conditioned electrical power for the ultraviolet lamp is obtained during disinfection periods. Since the electronics of the UV lamp driver is well-known in the trade, it is not described here. A protective shield cover 45 completely covers the top parts of ultraviolet protective shield 4 including its four fixing arms 42A and 42B. On two opposite arms of the protective shield cover 45 there are body connection holes 46, which align with the two body connection holes 43 on the fixing arms 42A, through which two fixing screws are applied.

Top cover 2 is placed above the reflection cup 3 and on top of the center shell 50. There are several disinfection cell holes 21 on the cover body 20, which allow passage tubes 23 to extend into disinfection cells 35, leading objects to be disinfected into the disinfection cells 35. Close to the rim on the bottom side of the top cover 2 there are two downward extensions whose lower parts are the locking hooks 24, which lock respectively into the cover locking slots 53. The locking hooks 24 first enter the wider end of the cover locking slots 53. When top cover 2 is turned in the clockwise direction, the locking hooks 24 move towards the narrower ends of the cover locking slots 53. Thus the hooks on the bottom of locking hooks 24 press against the inner ceiling near the cover locking slots 53, locking the top cover 2 and the device body 5 together. Additionally, on the bottom side of the top cover 2 near two of the disinfection cell holes 21, there are two downward extensions whose lower parts are the triggering hooks 22. After the top cover 2 and the center body 50 are locked together, the hooks at the bottom of the two triggering hooks 22 are respectively inserted into the triggering hook accepting slots at the top part of the two supporting poles 13B and the fixing arms 42B.

Figure 4:
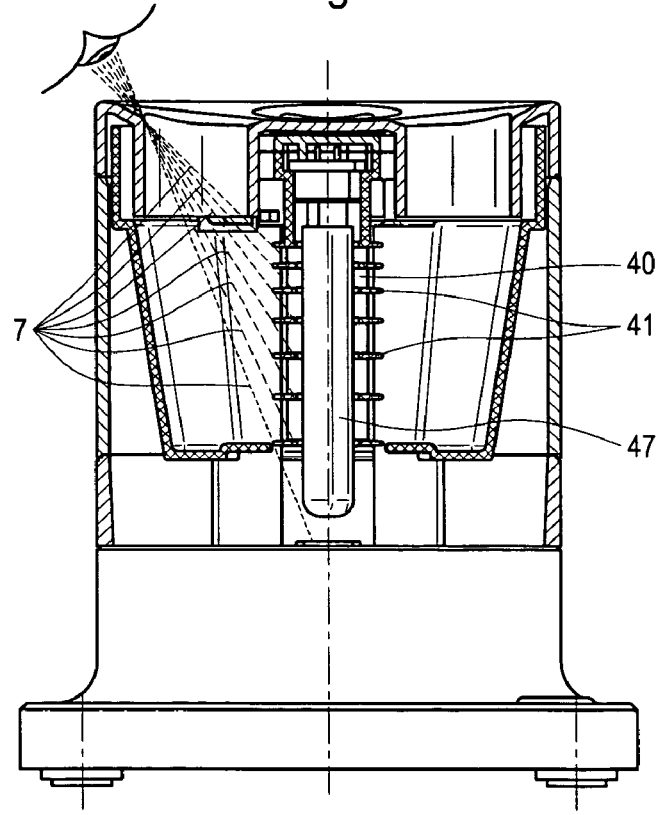
FIG. 4 is an illustration of the mechanism for the ultraviolet disinfection device in FIG. 3 to prevent the ultraviolet light generated by the ultraviolet lamp from leaking directly out of the device.
Figure 5:
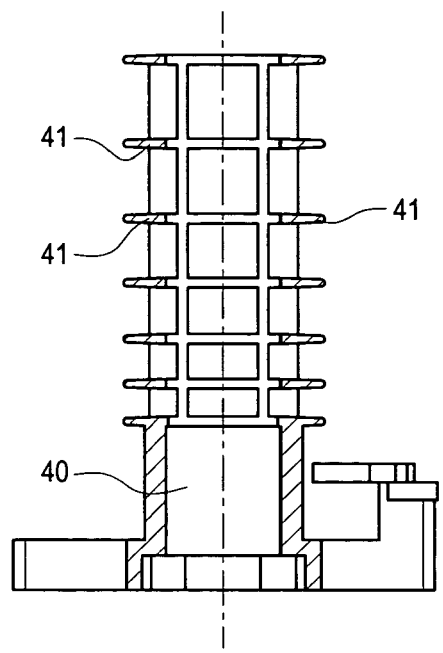
FIG. 5 is a sectional elevation view of the protective shield of the ultraviolet disinfection device that is shown in FIG. 2.

Please then refer to FIG. 4 and FIG. 5. FIG. 4 illustrates how the ultraviolet protective shield 4 of the ultraviolet disinfection device 100 prevents the ultraviolet light generated by the ultraviolet lamp 47 from leaking directly out of the device. FIG. 5 is a sectional elevation view of the ultraviolet protective shield 4. The ultraviolet protective shield 4 is made of a tough and strong material that is opaque to ultraviolet light and may be transparent, translucent or opaque to visible light. The stack of ring-shaped circular slats 41 of the ultraviolet protective shield 4 surrounds the ultraviolet lamp 47. The vertical thickness of the ring-shaped circular slats 41 is preferably as small as possible to minimize blockage of the ultraviolet light rays that shine into the disinfection cells 35, but thick enough to provide the required mechanical strength. To determine the appropriate thickness, factors such as the strength of the material, the fabrication method, the actual size of the shield and the overall cost allowed have to be considered. This embodiment employs injection molding of polycarbonate (PC) resin with stabilizer against UV added. For an outer diameter of 20 mm for the slats 41, it is found that the optimal vertical thickness of the slats 41 is slightly less than 1 mm around the inner circumference of the circular slats and progressively reduced to about 0.5 mm around the outer circumference.

The various levels of horizontal slats 41 are linked together and kept at strategic vertical spacing by the said thin vertical links. The horizontal slats 41 are said to be strategically spaced because the spacing density is not uniform for all the various levels: densest at the top level and progressively less dense for the lower levels (see FIG. 3). The specific horizontal width of each slat 41 in the stack and the specific vertical spacing of that slat from its neighbors are carefully selected so that all the slats in the stack together form a complete blockage against the ultraviolet light rays generated by the ultraviolet lamp 47 in all possible direct paths leading to the user's eyes through the disinfection cell holes 21 of the top cover 2, while the number of slats 41 in the stack is minimized so that the blockage effect is very little for the light rays that enter the disinfection cells 35. The vertical spacing of the different levels of the slats is not uniform because for any fixed point of view above any of the disinfection cell holes 21, the angle of view for a point at the ultraviolet lamp 47 varies with the vertical position of that point. By simple trigonometry, the optimal spacing of the different levels of the slats so, as to form a good-enough complete shield against the direct leakage of ultraviolet light rays can be worked out. As shown in FIG. 4, the slats prevent the ultraviolet light 7 generated by the ultraviolet lamp 47 from leaking through the disinfection cell holes 21 into the user's eyes. At the same time, most of the ultraviolet light is allowed to pass through the space between the slats 41 to reach the disinfection cells 35 and shine onto the major parts of the objects to be disinfected if the latter are inserted into the disinfection cells 35.

Figure 7:
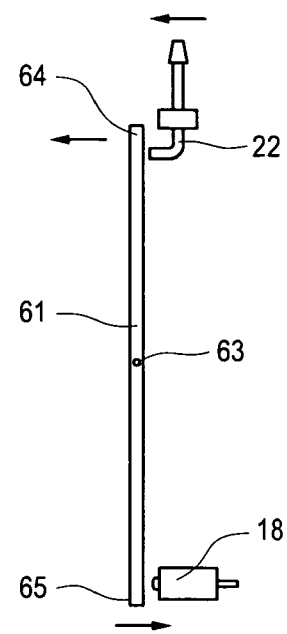
FIG. 7 illustrates the operation of the mechanical triggering device that is placed inside one of the supporting poles, which is shown in FIG. 6.

Please refer to FIG. 6 which is a perspective sectional view along the axis 6-6 of FIG. 1. In FIG. 6, a supporting pole 13B is sectioned to show its interior where the mechanical triggering device 6 is accommodated. As already described in a previous paragraph, the mechanical triggering device 6 consists of the pivot supporting frame 60 and the trigger plank 61. The pivot supporting frame 60 keeps the trigger plank 61 in the proper position and provides a pivot axis for the trigger plank 61 to turn about. After the top cover 2 is placed correctly to cover the device body 5, turning the top cover 2 in the clockwise direction will lock the top cover 2 and the device body 5 together. The two triggering hooks 22 will also be inserted respectively into the triggering hook accepting slots at the top part of supporting poles 13B and fixing arms 42B. As shown in FIG. 7, triggering hook 22 pushes the top part 64 of the trigger plank 61 to the left. Thus the bottom part 65 of trigger plank 61 moves to the right because of the leverage action. When it presses the micro-switch 18 inside the base 1, the circuit in the circuit board 15 is turned on, and the automatic disinfection program starts to cycle.

Figure 8:
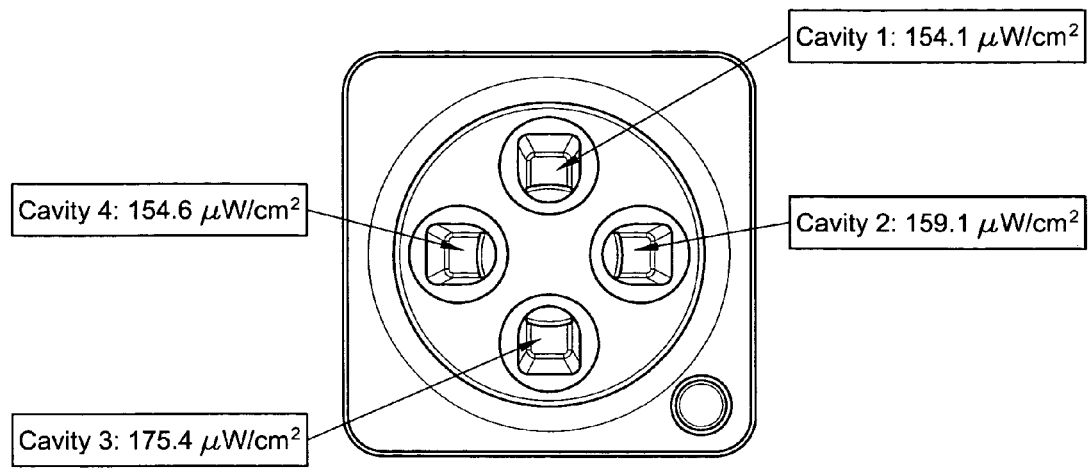
FIG. 8 illustrates the strength of the ultraviolet light that leaks from a preferred embodiment of the ultraviolet disinfection device right outside the disinfection cell holes with the protective shield removed.
Figure 9:
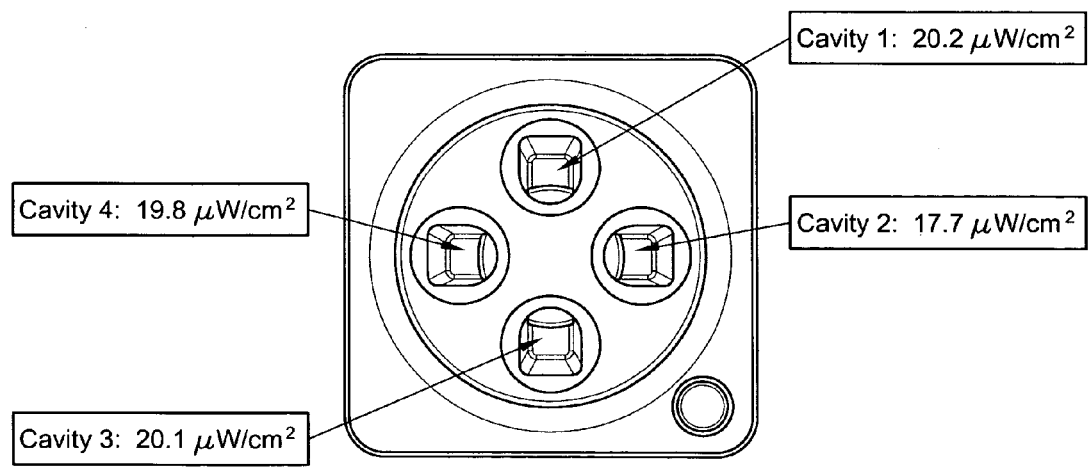
FIG. 9 illustrates the strength of the ultraviolet light that leaks from a preferred embodiment of the ultraviolet disinfection device right outside the disinfection cell holes with the protective shield installed.
Figure 10:
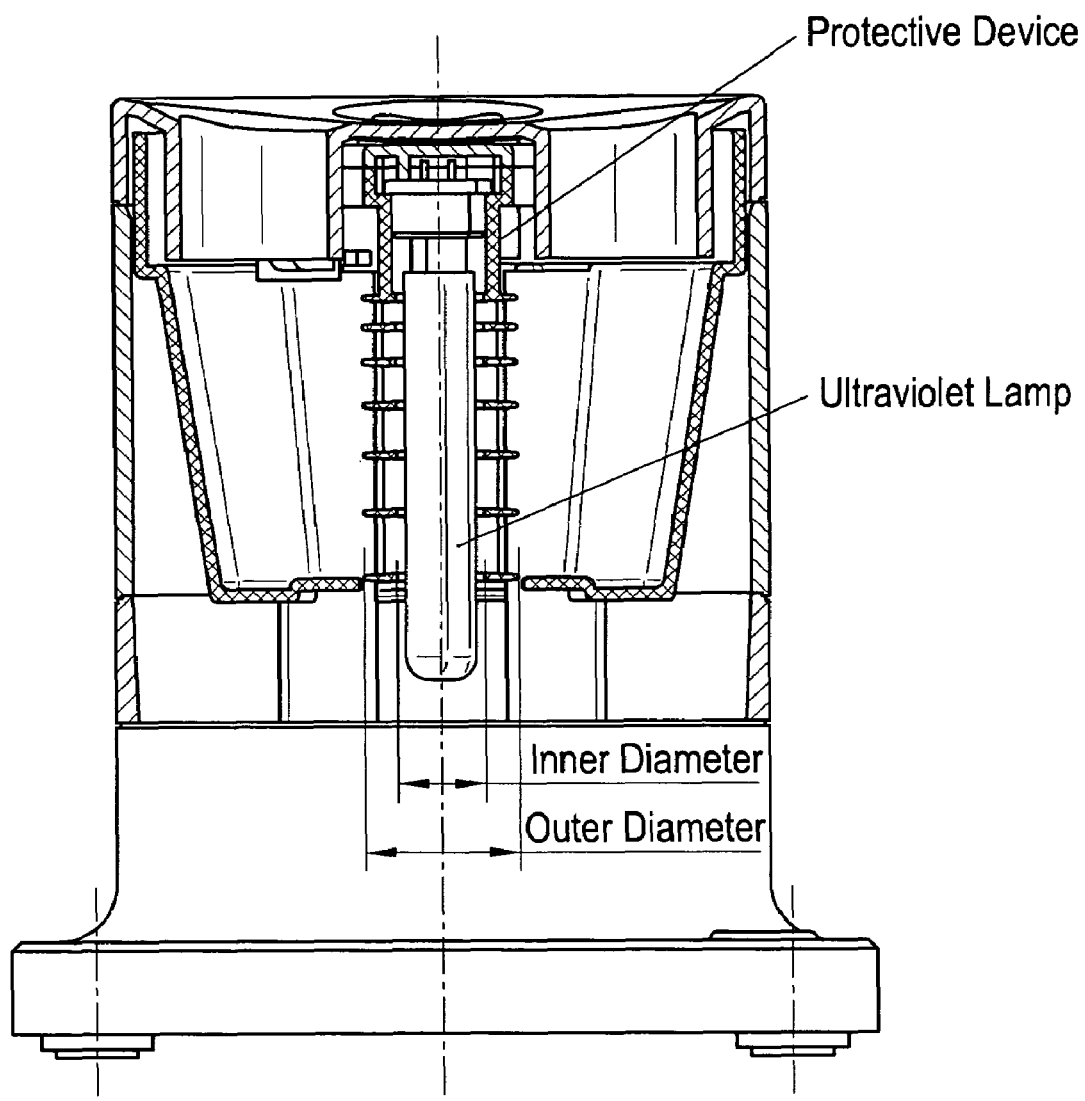
FIG. 10 shows a cross section of the ultraviolet disinfection device.
Figure 11:
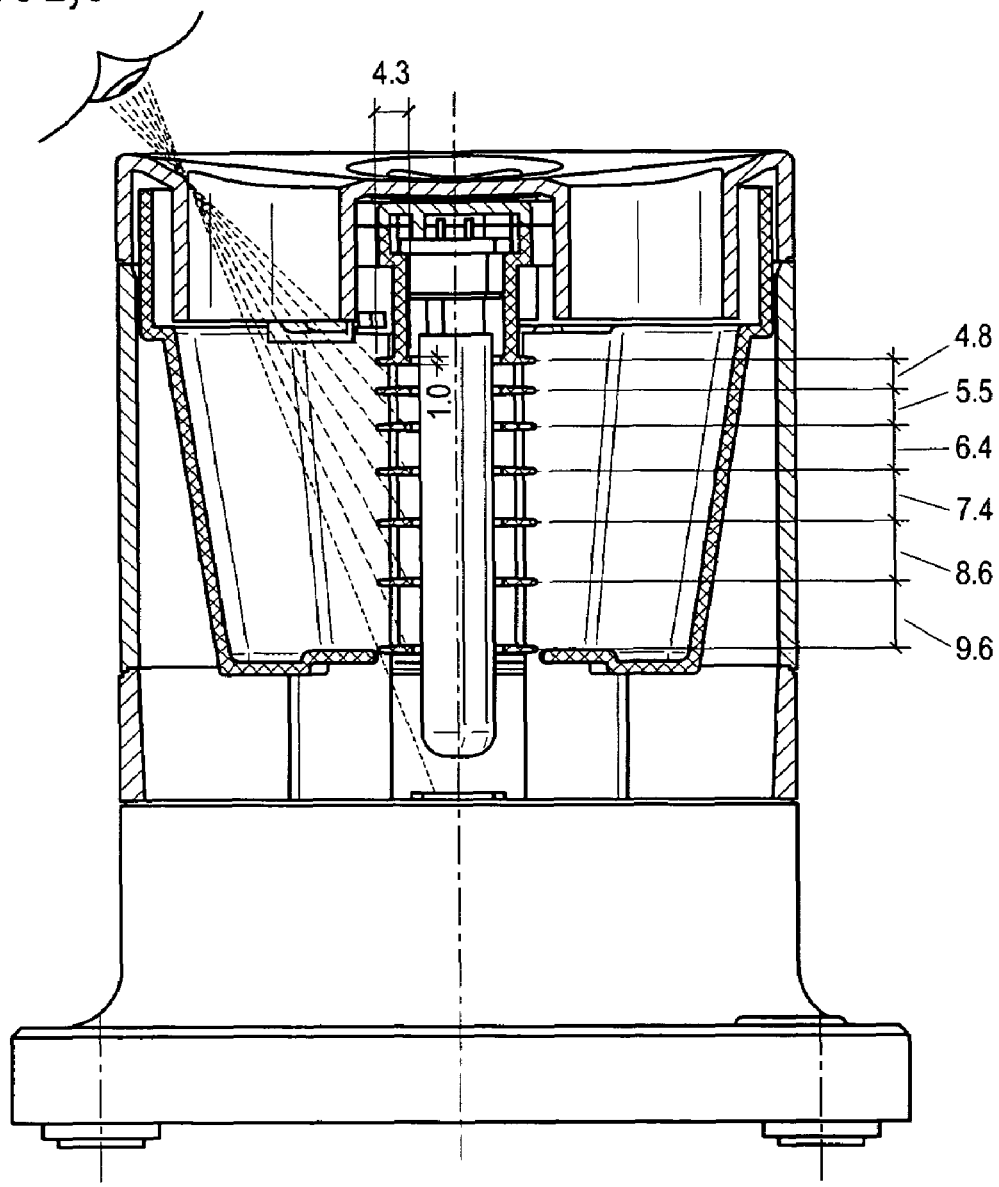
FIG. 11 shows a cross section of the ultraviolet disinfection device with an exemplary arrangement of horizontal slats.
Figure 12:
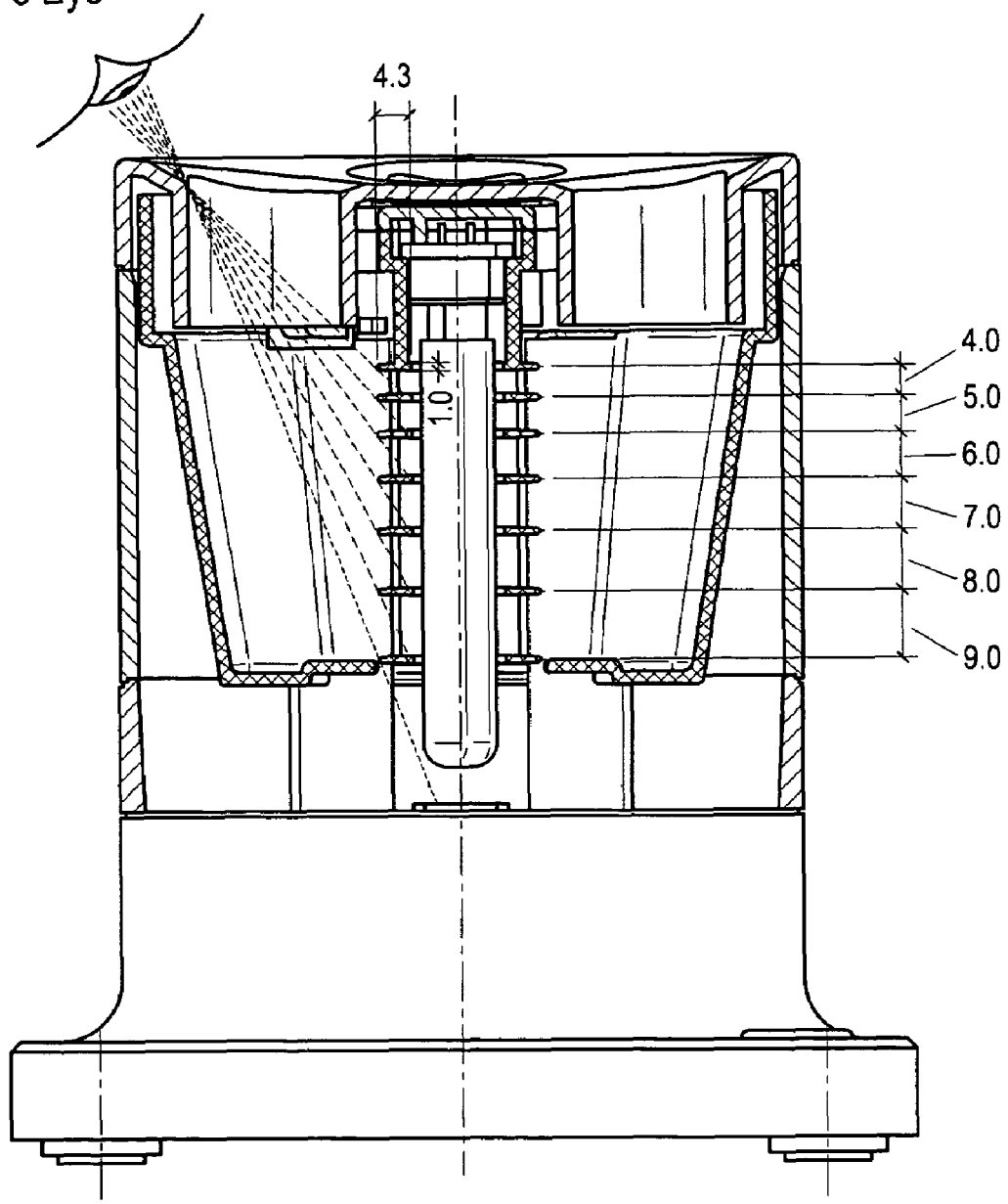
FIG. 12 shows a cross section of the ultraviolet disinfection device with another exemplary arrangement of horizontal slats.

Finally, please refer to FIG. 8 and FIG. 9. They illustrate respectively the strength of the ultraviolet light that leaks from this ultraviolet disinfection device 100 right outside the disinfection cell holes 21 before and after installation of the ultraviolet protective shield 4. In FIG. 8, where the ultraviolet disinfection device 100 is without the ultraviolet protective shield 4, the ultraviolet strength readings right outside the disinfection cell holes 21 average to 160 $\mu Wcm^{-2}$. But when the ultraviolet disinfection-device 100 is with the ultraviolet protective shield 4 installed inside, the ultraviolet strength readings right outside the disinfection cell holes 21, as shown in FIG. 9, average to 20 $\mu Wcm^{-2}$. This demonstrates that the ultraviolet protective shield 4 can substantially reduce the leakage of the ultraviolet light from the ultraviolet disinfection device 100.

Based on the abovementioned structure, ultraviolet disinfection device 100 utilizes a simple design to automatically disinfect long objects such as toothbrushes and chopsticks by simply inserting the objects into the disinfection cells 35 of this device 100. It is very easy to disinfect personal belongings. By utilizing the ultraviolet protective shield 4 around the ultraviolet lamp 47 with a shield body 40, this design both provides sufficient disinfection power and reduces substantially the leakage of ultraviolet light that may otherwise hurt the user's eyes. This ultraviolet disinfection device 100 is both convenient and safe to use, and is also good for the user's health.

What is claimed:

1. An ultraviolet disinfection device comprising:
   (a) a body for accepting at least one object to be disinfected, said body containing at least one germicidal UV lamp;
   (b) a top cover that is supported by said body, said top cover having at least one opening for accepting the objects to be disinfected into at least one disinfecting cell; said top cover having at least one triggering hook for extending into said body of the ultraviolet disinfection device;
   (c) at least one protective shield that surrounds said at least one germicidal UV lamp, said protective shield being made of a material that is opaque to ultraviolet light, said protective shield having a hollow body and a stack of parallel slats with spacing in between the said slats, said slats of said stack being connected by at least one link extending from the said body of said protective shield, the center of each said slat having a hole larger than the diameter of said UV lamp, the hollow center of the said body of said protective shield and said holes at the center of all layers of slats altogether forming a cavity for accommodating the said UV lamp, at least a portion of the light-emitting length of said at least one germicidal UV lame being surrounded by said stack of slats,
   wherein said protective shield prevents direct leakage of UV light generated from said germicidal UV lamp through said at least one opening on said top cover;
   wherein said disinfection device further includes at least one additional feature selected from the group consisting of:
   (d) the density of vertical spacing of said horizontal slats of said protective shield is lower at the bottom, and higher on the top;
   (e)
      i. said body of the device has at least one supporting pole extended unwards from the bottom;
      ii. said protective shield has a least one fixing arm protruding outwards from the body of said protective shield;
      iii. said at least one fixing arm of said protective shield is mounted on top of said at least one supporting pole, and said top cover has at least one positioning and locking hook extending downwards from the bottom surface of said top cover;
   (f) wherein the protective shield reduces the ultraviolet light emitted from the device eight fold; and
   (g) wherein the protective shield reduces the ultraviolet light emitted from the device to 20 $\mu Wcm^{-2}$.

2. An ultraviolet disinfection device comprising:
   (a) a body for accepting at least one object to be disinfected, said body containing at least one gennicidal UV lamp;
   (b) a top cover that is supported by said body, said top cover having at least one opening for accepting the objects to be disinfected into at least one disinfecting cell; said top cover having at least one triggering hook for extending into said body of the ultraviolet disinfection device;
   (c) at least one protective shield that surrounds said at least one germicidal UV lamp, said protective shield being made of a material that is opaque to ultraviolet light said protective shield having a hollow body and a stack of parallel slats with spacing in between the said slats, said slats of said stack being connected by at least one link extending from the said body of said protective shield, the center of each said slat having a hole larger than the diameter of said UV lamp, the hollow center of the said body of said protective shield and said holes at the center of all layers of slats altogether forming a cavity for accommodating the said UV lamp, at least a portion of the light-emitting length of said at least one germicidal UV lamp being surrounded by said stack of slats,
   wherein said protective shield prevents direct leakage of UV light generated from said germicidal UV lamp through said at least one opening on said top cover;
   (d) said top cover has at least one positioning and locking hook extending downwards from the bottom surface of said top cover;
   (e) there are cover locking slots correspondingly located on the top surface of said body to accept said at least one positioning mid locking hook;
   (f) the shape of said cover locking slots is irregular, being wider at one end and narrower at the other end;
   (g) when said top cover is engaged with said body of the device, said at least one positioning and locking hook is first inserted into the wider end of said slot;
   (h) when said top cover is then turned in the correct direction, said at least one positioning and locking hook moves towards the narrower end of said slot, resulting in said hook pressing on the ceiling near the narrower end of said slot, making said top cover and said body of the device locked together.

3. An ultraviolet disinfection device comprising:
   (a) a body for accepting at least one object to be disinfected, said body containing at least one germicidal UV lamp;
   (b) a top cover that is supported by said body, said top cover having at least one opening for accepting the objects to be disinfected into at least one disinfecting cell; said top cover having at least one triggering hook for extending into said body of the ultraviolet disinfection device
   (c) at least one protective shield tat surrounds said at least one germicidal UV lamp, said protective shield being made of a material that is opaque to ultraviolet light, said protective shield having a hollow body and a stack of parallel slats with spacing in between the said slats, said slats of said stack being connected by at least one link extending from die said body of said protective shield, the center of each said slat having a hole larger than the diameter of said UV lamp, the hollow center of the said body of said protective shield and said holes at the center of all layers of slats altogether forming a cavity for accommodating the said UV lamp, at least a portion of the light-emitting length of said at least one germicidal UV lamp being surrounded by said stack of slats, wherein said protective shield prevents direct leakage of UV light generated from said germicidal UV lamp through said at least one opening on said top cover
   (d) a reflection cup mounted within the body of said device beneath said top cover, said reflection cup being removable by a user;
   (e) said body of the device has a least one supporting pole extended upwards from the bottom;
   (f) said protective shield has a least one fixing arm protruding outwards from the body of said protective shield;
   (g) said at least one fixing arm of said protective shield is mounted on top of said at least one supporting pole;
   (h) said top cover has at least one positioning and locking hook extending downwards from the bottom surface of said top cover; and
   (i) said reflection cup has at least one hole, appropriately shaped, at the bottom to allow passage of said at least one supporting pole through said at least one hole when said reflection cup is placed in said body of the device.

4. The device of claim 2 further wherein a micro-switch in said body of the device is coupled to at least one of said at least one triggering hook of said removable top cover such that when said removable top cover is removed or not placed properly, no power is supplied to said gennicidal UV lamp.

5. The device of claim 4, further comprising:
(a) a trigger plank mounted within said body of said device by means of a pivot the axis of which passes through said trigger plank somewhere around its mid-length, the lower tip of said trigger plank being coupled to the said micro-switch while the upper tip of said trigger plank being coupled to said at least one triggering hook of said removable top cover, placing said top cover properly on top of said body of said device and then turning said top cover in the correct direction resulting in making the said at least one triggering hook of said removable top cover press against the upper tip of said trigger plank, consequently, because of leverage action, making the lower tip of said trigger plant press against said micro-switch which then makes electrical connection to allow turning on of said at least one germicidal UV lamp, whereby when said top cover is removed, improperly placed or not turned in the correct direction sufficiently to activate said micro-switch switch, no power is supplied to said germicidal UV lamp.

* * * * *